(12) United States Patent
Zhang et al.

(10) Patent No.: US 12,083,231 B2
(45) Date of Patent: Sep. 10, 2024

(54) STARCH-BASED DOUBLE-LOADED FUNCTIONAL NANO PARTICLE AS WELL AS PREPARATION METHOD AND APPLICATION

(71) Applicant: Hefei University of Technology, Hefei (CN)

(72) Inventors: Bao Zhang, Hefei (CN); Wenjie Liu, Hefei (CN); Han Tao, Hefei (CN); Xiaolong Li, Hefei (CN); Pin Chen, Hefei (CN); Rumeng Wang, Hefei (CN)

(73) Assignee: HEFEI UNIVERSITY OF TECHNOLOGY, Hefei (CN)

( * ) Notice: Subject to any disclaimer, the term of this patent is extended or adjusted under 35 U.S.C. 154(b) by 158 days.

(21) Appl. No.: 17/715,970

(22) Filed: Apr. 8, 2022

(65) Prior Publication Data

US 2023/0042688 A1 Feb. 9, 2023

(30) Foreign Application Priority Data

Aug. 6, 2021 (CN) .......................... 202110902696.7

(51) Int. Cl.
| | | |
|---|---|---|
| A61K 9/51 | (2006.01) | |
| A23P 10/30 | (2016.01) | |
| B05D 1/00 | (2006.01) | |
| C07K 14/465 | (2006.01) | |
| C07K 19/00 | (2006.01) | |
| C08B 30/18 | (2006.01) | |
| C12P 19/04 | (2006.01) | |
| C12P 19/16 | (2006.01) | |
| C12P 21/06 | (2006.01) | |

(52) U.S. Cl.
CPC ............ *A61K 9/5192* (2013.01); *A23P 10/30* (2016.08); *A61K 9/5161* (2013.01); *B05D 1/007* (2013.01); *C07K 14/465* (2013.01); *C07K 19/00* (2013.01); *C08B 30/18* (2013.01); *C12P 19/04* (2013.01); *C12P 19/16* (2013.01); *C12P 21/06* (2013.01)

(58) Field of Classification Search
None
See application file for complete search history.

(56) References Cited

U.S. PATENT DOCUMENTS

| | | | | |
|---|---|---|---|---|
| 2007/0031398 A1* | 2/2007 | Miller | ................... | A61K 31/198 424/94.63 |
| 2009/0110739 A1* | 4/2009 | Lacko | .................. | A61K 9/5123 514/459 |

FOREIGN PATENT DOCUMENTS

WO WO-2020061683 A1 * 4/2020 ................ A23J 1/08

OTHER PUBLICATIONS

Wang et al.; "Development of 'all natural' layer-by-layer redispersible solid lipid nanoparticles by nano spray drying technology," 2016; ELSEVIER; European Journal of Pharmaceutics and Biopharmaceutics, vol. 107, pp. 273-285. (Year: 2016).*
Xie et al.; "Insight into interfacial adsorption behavior of high-density lipoprotein hydrolysates regulated by carboxymethyl dextrin and in vitro digestibility of curcumin loaded high internal phase emulsions," 2023; ELSEVIER; Food Chemistry, vol. 400, pp. Article 134006, pp. 1-12. (Year: 2023).*
Liu et al.; "Self-Assembled Micellar Nanoparticles by Enzyme Hydrolysis of High Density Lipoprotein for the Formation and Stability of High Internal Phase Emulsions," Aug. 2021, ACS; Journal of Agricultural and Food Chemistry, vol. 69, pp. 11015-11025. (Year: 2021).*
Zhang et al.; "Emulsifying and emulsion stabilizing properties of hydrolysates of high-density lipoprotein from egg yolk," 2021; ELSEVIER, Food Chemistry, vol. 369, article 130891, pp. 1-10. (Year: 2021).*
Feng et al.; "Enhanced Chemical Stability, Intestinal Absorption, and Intracellular Antioxidant Activity of Cyanidin-3-O-glucoside by Composite Nanogel Encapsulation," 2019; ACS; Journal of Agricultural and Food Chemistry, vol. 67, pp. 10432-10447. (Year: 2019).*
Yang et al.; "Alkali induced gelation behavior of low-density lipoprotein and high-density lipoprotein isolated from duck eggs," 2020, ELSEVIER; Food Chemistry, vol. 311, Article 125952, pp. 1-9. (Year: 2020).*
Zhou et al.; "Characterization of high density lipoprotein from egg yolks and its ability to form nanocomplexes with chitosan as natural delivery vehicle," 2018; ELSEVIER; Food Hydrocolloids, vol. 77, pp. 204-211. (Year: 2018).*
Gao et al.; "Effect of enzymatic hydrolysis on heat stability and emulsifying properties of egg yolk," 2019, ELSEVIER; Food Hydrocolloids, vol. 97, Article 105224, pp. 1-7. (Year: 2019).*

(Continued)

*Primary Examiner* — Tigabu Kassa
*Assistant Examiner* — Ivan A Greene
(74) *Attorney, Agent, or Firm* — Bayramoglu Law Offices LLC (57) ABSTRACT

The preparation method of a starch-based double-loaded functional nanoparticle includes: performing restrictive hydrolysis treatment on egg high-density lipoprotein using proteases to obtain the polypeptide; performing self-assembling on a mixed system containing the polypeptide and quercetin under the alkaline condition to form a micelle nanoparticle; performing covalent grafting reaction on a mixed system containing the micelle nanoparticle and anthocyanin under the alkaline condition to form a graft; and electrostatically compounding carboxymethyl dextrin with the graft to obtain the starch-based double-loaded functional nanoparticle. In the preparation method, raw materials derived from natural sources are used, and the self-assembled colloid nanoparticle with good properties can be obtained by adjusting the pH without any organic reagents. The obtained product has a nanoparticle size, has high antioxidant activity and stability against environmental stress, and can be widely applied to the fields of delivery of nutrients, stabilization of biologically active substances and the like.

16 Claims, 8 Drawing Sheets

(56) References Cited

OTHER PUBLICATIONS

Tang et al.; "Effect of enzymatic hydrolysis on the solubility of egg yolk powder from the changes in structure and functional properties," 2019; ELSEVIER; LWT-Food Science and Technology, vol. 110, pp. 214-222. (Year: 2019).*
Chen et al.; "Adsorption Behavior of Carboxymethyl Starch on Titanium Dioxide Surfaces," 2011; Pleiades Publishing; Colloid Journal, vol. 73, No. 2, pp. 267-274. (Year: 2011).*
Meng et al.; "Zein/carboxymethyl dextrin nanoparticles stabilized Pickering emulsions as delivery vehicles: Effect of interfacial composition on lipid oxidation and in vitro digestion," 2020; ELSEVIER; Food Colloids, vol. 108, Article 106020, pp. 1-11. (Year: 2020).*
Li et al.; "Fabrication of chitosan hydrochloride and carboxymethyl starch complex nanogels as potential delivery vehicles for curcumin," 2019; ELSEVIER; Food Chemistry, vol. 293, pp. 197-203. (Year: 2019).*
Busatto et al.; "Lipoprotein-based drug delivery," 2020; ELSEVIER, Advanced Drug Delivery Reviews, vol. 159, pp. 377-390. (Year: 2020).*
Lacko et al.; "Drug delivery via lipoprotein-based carriers: answering the challenges in systemic therapeutics," 2012, Future Science Ltd .; Therapeutic Delivery, vol. 3, No. 5, pp. 599-608. (Year: 2012).*

\* cited by examiner

STARCH-BASED DOUBLE-LOADED FUNCTIONAL NANO PARTICLE AS WELL AS PREPARATION METHOD AND APPLICATION

CROSS REFERENCE TO RELATED APPLICATIONS

This application claims priority to Chinese Patent Application No. 202110902696.7 entitled "STARCH-BASED DOUBLE-LOADED FUNCTIONAL NANO PARTICLE AS WELL AS PREPARATION METHOD AND APPLICATION, filed on Aug. 6, 2021, the entire contents of which are incorporated herein by reference.

TECHNICAL FIELD

The present application relates to a starch-based double-loaded functional nanoparticle as well as a preparation method and application, belonging to the field of deep processing technologies of agricultural products.

BACKGROUND

Proteins have the characteristics of rich resources, low price and rich nutrition. At the same time, they also have some biological activities. They are preferred raw materials for protein-based nano delivery carriers. However, most of the proteins have spherical protein structures, and their hydrophobic cores are buried in compact tertiary structures in most cases, which are not conducive to the binding of the hydrophobic cores to hydrophobic active substances. In addition, different protein sources have different effects on formation mechanisms and functions of their nano materials. The polypeptides prepared by treating the proteins via a biological enzymatic method not only have many physiological activities (such as antioxidant, antihypertensive and antibacterial) that the proteins do not have, but also have significantly increased water dispersion so that they can be dispersed and stable in a wide pH range. Meanwhile, as a class of compounds between amino acids and proteins, polypeptides also have biological amphiphilicity. The hydrophobic groups existing in polypeptides still have high reaction activity and easily interact with hydrophobic active factors, and therefore, the polypeptides have great potential as new food functional factor embedding carriers.

At present, researchers have proposed a variety of methods to prepare functional nano materials by utilizing polypeptides. For example, one of the common methods is a pH driven method, which is also called a pH cycle or pH transfer method. It usually refers to a process of adjusting the pH of a system from neutral to extremely acidic or alkaline, and then adjusting the pH back to be neutral or making the pH neutral. By mixing extremely acidic and alkaline dispersions, the final system is close to neutral so as to induce molecules to generate structural changes and interaction. CN112273654A discloses a method for preparing soybean proteolytic aggregates embedded curcumin nanoparticles by the pH driven method. The prepared nanoparticles have the advantages of good stability, high loading capacity and good biocompatibility. However, the existing preparation processes of polypeptide-based functional nano materials often need to involve organic solvents, chemical treatments and complex processes and equipment in the process of implementation, which has high cost and is difficult to popularize and apply. Moreover, most of the prepared products have single function and their stability and other properties need to be improved.

SUMMARY

The main objective of the present application is to provide a starch-based double-loaded functional nanoparticle as well as a preparation method and application to overcome the defects in the prior art.

In order to achieve the above objective, the technical solution adopted by the present application is as follows:

The embodiments of the present application provide a preparation method of a starch-based double-loaded functional nanoparticle, comprising:

(1) performing restrictive hydrolysis treatment on egg high-density lipoprotein by using proteases, and then isolating and purifying by using dialysis and ethanol precipitation methods to obtain polypeptides;

(2) performing self-assembling on a mixed system containing the polypeptides and quercetin under the alkaline condition to form a micelle nanoparticle;

(3) performing covalent grafting reaction on a mixed system containing the micelle nanoparticle and anthocyanin in an alkaline environment to form a graft; and (4) compounding carboxymethyl dextrin with the graft through electrostatic interaction under the acidic condition to obtain the starch-based double-loaded functional nanoparticle.

In some embodiments, step (1) comprises: the restrictive hydrolysis treatment is performed on egg high-density lipoprotein with any one or more of trypsin, alkaline protease and neutral protease. After the restrictive hydrolysis treatment is completed, the hydrolysates are dialyzed at 0-4° C. for more than 48 h. The cutoff molecular weight of the adopted dialysis bag is above 5000 Daltons. Then the dialyzed product is mixed with ethanol so that the final concentration of ethanol in a mixture is 10-25%, and the obtained mixture is centrifuged to remove the precipitate. The supernate is subjected to freeze drying and treated at an oven of 75-90° C. for 5-20 min to obtain the polypeptide.

In some embodiments, step (2) comprises: the polypeptide and quercetin are dispersed into water to form a mixed system, NaCl is added to adjust the ionic strength of the mixed system, then the mixed system is adjusted to be alkaline and stirred to react, so that the polypeptide and the quercetin are subjected to self-assembling to form the micelle nanoparticle.

In some embodiments, step (3) comprises: a solution of the micelle nanoparticle is mixed with an anthocyanin solution to form a mixed system, the pH of the mixed system is adjusted to be alkaline, and the above mixed system is continuously stirred to undergo a covalent grafting reaction, thereby forming the graft.

In some embodiments, step (4) comprises: the solution of the graft is stirred and mixed with a solution of carboxymethyl dextrin, and meanwhile the pH of the mixed system is adjusted to 3, thereby obtaining the starch-based double-loaded functional nanoparticle.

In some embodiments, the carboxymethyl dextrin adopts a homogeneous carboxymethyl dextrin with a substitution degree of 0.3-0.7.

In the embodiments of the present application, the egg high-density lipoprotein is subjected to restrictive hydrolysis by using any one or more of trypsin, alkaline protease and neutral protease so that its internal hydrophobic group is exposed, and a polypeptide (named EHT) having better solubility, surface hydrophobicity and emulsifying characteristic is formed. The polypeptide can be subjected to self-assembling under different conditions and can bind to quercetin (Que) through hydrophobic interactions under the alkaline condition without organic solvents, which is simple and safe; furthermore, the self-assembled quercetin-polypeptide composite micelle nanoparticle (that is, the aforementioned micelle nanoparticle, hereinafter also referred to as a Que-EHT composite micelle nanoparticle) formed by compounding the polypeptide with quercetin can be covalently grafted with anthocyanin (C3G) in the alkaline environment, this process is simple and environmentally friendly, and the obtained quercetin-polypeptide-anthocyanin graft (hereinafter referred to as a Que-EHT-C3G graft) can load biological active substances with different polarities, for example, the quercetin-polypeptide-anthocyanin graft can be compounded with carboxymethyl dextrin (CMD) through electrostatic interaction under the acidic condition to obtain a double-loaded self-assembled colloid nanoparticle with a core-shell structure and a double-loaded function (i.e., the aforementioned starch-based double-loaded functional colloid nanoparticle).

The embodiments of the present application also provide the starch-based double-loaded functional nanoparticle prepared by the above method.

The embodiments of the present application also provide application of the starch-based double-loaded functional nanoparticle in the preparation of an antioxidant delivery system or foods.

Compared with the prior art, the raw materials required for the preparation process of the starch-based double-loaded functional colloid nanoparticle provided by the present application are all derived from natural sources, and the self-assembled colloid nanoparticle with good properties can be obtained by adjusting the pH without any organic reagents. The preparation method is simple in process, efficient, safe, and easy to product on large sale, and the obtained starch-based double-loaded functional colloid nanoparticle has significantly improved stability against environmental stress and excellent antioxidant activity and can be widely applied to the fields of delivery of nutrients, stabilization of biologically active substances and the like.

BRIEF DESCRIPTION OF THE DRAWINGS

For more clearly illustrating the embodiments of the present application or the technical solution in the prior art, the embodiments or the drawings required for description in the prior art will be simply described below. Obviously, the drawings in the description below are only some embodiments described in the present application, and other drawings can also be made by persons of ordinary skill in the art according to these drawings without creative efforts.

DESCRIPTION OF THE EMBODIMENTS

In view of the technical problems existing in the prior art, the inventor of this case proposed the technical solution of the present application through long-term research and lots of practices.

One aspect of the embodiment of the present application provides a preparation method of a starch-based double-loaded functional nanoparticle, comprising:
(1) performing restrictive hydrolysis treatment on egg high-density lipoprotein (HDL) with proteases, and then isolating and purifying by dialysis and an ethanol precipitation method to obtain the polypeptide;
(2) performing self-assembling on a mixed system containing the polypeptide and quercetin under the alkaline condition to form a micelle nanoparticle;
(3) performing covalent grafting reaction on a mixed system containing the micelle nanoparticle and anthocyanin in the alkaline environment to form a graft; and
(4) compounding carboxymethyl dextrin with the graft through electrostatic interaction to obtain the starch-based double-loaded functional nanoparticle.

In some embodiments, step (1) comprises: the restrictive hydrolysis treatment is performed on egg high-density lipoprotein by using any one or more of trypsin, alkaline protease and neutral protease, the temperature of the restrictive hydrolysis treatment is 30-55° C., the time of the restrictive hydrolysis treatment is 0.5-4.5 h, and the pH of the hydrolysis reaction system is 8.0-9.0, wherein the addition amount of the protease is 20-100 U/g of egg high-density lipoprotein.

In some embodiments, step (1) also comprises: after the restrictive hydrolysis treatment is completed, the hydrolysate is dialyzed at 0-4° C. for more than 48 h, the cutoff molecular weight of the adopted dialysis bag is above 5000 Daltons, then the dialyzed product is mixed with ethanol so that the final concentration of ethanol in the mixture is 10-25%, the above mixture is centrifuged to remove the precipitate, and the supernate is subjected to freeze drying and treated at an oven of 75-90° C. for 5-20 min to obtain the polypeptide.

Further, the time of dialysis is above 48 h, and the cutoff molecular weight of the adopted dialysis bag is above 5000 Daltons.

Further, the product obtained by dialysis is mixed with ethanol and stirred for 30 min, and then centrifuged at 4000 g for 20 min.

Further, in step (1), the hydrolysis degree of the egg high-density lipoprotein polypeptide obtained after the restrictive hydrolysis treatment is 6.7%-10%.

Further, the molecular weight of the polypeptide is 5-20 kDa.

In some more specific embodiments, EHT can be prepared by using the following method: 1 g of egg high-density lipoprotein is correctly weighed and dispersed into 20 mL of deionized water, the pH of the solution is adjusted to 8.0, the solution is heated in a water bath pot of 37° C. until the temperature is constant. A certain amount of trypsin, alkaline protease and neutral protease (50 U/g egg high-density lipoprotein) are added and uniformly stirred; the resulting mixture is hydrolyzed for 0.5-4.5 h under the temperature-constant water bath condition of 37° C., the hydrolysis degree of the hydrolysate is 6.7%-10%, and the molecular weight of the egg high-density lipoprotein hydrolysate is 5-10 kDa. Further, the hydrolysate is dialyzed at 0-4° C. for 48 h, the specification of the used cellulose dialysis bag is 5000 Daltons; the resulting mixture of the obtained hydrolysate and ethanol is centrifuged to remove the precipitate, and the supernate is subjected to freeze drying and treated in an oven of 80° C. for 10 min.

The egg high-density lipoprotein (HDL) used in the present application is the second largest lipoprotein in eggs, and has high protein content and good gel property. In the present application, after the restrictive hydrolysis treatment, the size, conformation and intermolecular/intramolecular acting forces of the HDL molecule change, so that functional groups are better exposed, and properties such as solubility, surface hydrophobicity and emulsification are all remarkably improved.

In some embodiments, step (2) comprises: the polypeptide and quercetin are dispersed into water to form a mixed system in which the concentration of the polypeptide is 10-50 mg/mL and a mass ratio of quercetin to polypeptide is 1:100-1:10, and NaCl is added to adjust the ionic strength of the mixed system to 80-120 mmol/L, then the pH of the mixed system is adjusted to 10-12, and the mixed system is stirred for 30-60 min, so that the polypeptide and the quercetin are subjected to self-assembling to form the micelle nanoparticle.

The quercetin is a natural flavonoid which has antioxidant, anticancer, anti-inflammatory and anti-atherosclerotic activities. However, the widespread application of the quercetin in many foods is limited due to its low water solubility, chemical instability and poor bioavailability. In short-term strong alkaline treatment, the quercetin can be deprotonated, and the water solubility is significantly increased with negligible degradation. Based on the pH-dependent solubility of the quercetin and the self-assembly characteristic of the polypeptide, a polypeptide-based self-assembled micelle nanoparticle loaded with quercetin is prepared.

In some embodiments, step (3) comprises: a solution of the micelle nanoparticle is mixed with an anthocyanin solution to form a mixed system with the pH of 9.0-9.5, and the above mixed system is continuously stirred at the speed of 300-600 rpm to undergo a covalent grafting reaction for 20-30 h, thereby forming the graft.

Further, a mass ratio of the quercetin to the anthocyanin is 1:2-2:1.

In some embodiments, step (3) also comprises: after the covalent grafting reaction is completed, the pH of the mixture is adjusted to be neutral, and then the mixture is dialyzed at 0-4° C. for 20-24 h to obtain the graft, wherein the cutoff molecular weight of the adopted dialysis bag is 3500-4000 Daltons.

In some more specific embodiments, a quercetin-polypeptide-anthocyanin graft can be prepared by using the following method: quercetin powder and EHT are dispersed into water in a mass ratio of 1:100-1:10, wherein the concentration of EHT is 10-50 mg/mL, and NaCl is added to adjust the ionic strength of the mixed system to 80-120 mmol/L, then the pH of the mixed system is adjusted to 12, and the above solution is stirred and mixed for 30-60 min. A certain mass of anthocyanin powder is added into the above mixed solution, so that a mass ratio of the quercetin and the anthocyanin is 1:2-2:1. The pH of the solution is adjusted to 9.0, and the solution is stirred at 500 rpm for 24 h; a 1 M HCl solution is used to adjust the pH of the mixed solution to 7. After the modification treatment is completed, the reaction system is dialyzed for 20-24 h, and the molecular weight cutoff of the dialysis bag is 3500-4000 Daltons.

Anthocyanin is present in a large class of natural plants and considered as an ideal natural colorant and may provide a variety of health benefits such as antioxidant, anticancer, antimutagenic and anti-inflammatory effects. However, the utilization of the natural anthocyanin is still limited by some physical and chemical factors, such as pH and temperature. In the present application, the physical stability, antioxidant activity and bioavailability of the anthocyanin can be improved by covalently binding the anthocyanin to the polypeptide.

In some embodiments, step (4) comprises: the solution of the graft is stirred and mixed with a solution of carboxymethyl dextrin, and meanwhile an acidic solution is added to adjust the pH of the mixed system to 3, thereby obtaining the starch-based double-loaded functional nanoparticle.

Further, a mass ratio of the polypeptide to the carboxymethyl dextrin is 4:1-1:4.

In some more specific embodiments, the solution system containing the quercetin-polypeptide-anthocyanin graft can be mixed with the carboxymethyl dextrin solution, wherein the mass ratio of the polypeptide to the carboxymethyl dextrin is 4:1-1:4, 1 mol/L HCl solution is dropwise added while stirring to adjust the pH of the obtained mixed solution to 3, and the mixed solution is subjected to freeze drying to obtain a starch-based double-loaded functional nanoparticle with a core-shell structure.

In the present application, negatively charged carboxymethyl dextrin molecules are compounded with positively charged quercetin-polypeptide-anthocyanin grafts through electrostatic interaction under the acidic condition to form the starch-based double-loaded functional nana particle with the core-shell structure. The external carboxymethyl dextrin layer can enhance the rigidity of the nanoparticle, and the polysaccharide side chains can provide greater steric hindrance for the composite particles, enhancing the stability of the particles and protection of the embedded bioactive components.

In some embodiments, a method for preparing the carboxymethyl dextrin comprises:

alkalizing dextrin with a homogeneous polymerization degree at 35-40° C. for 3-5 h to obtain alkalized dextrin; and etherifying a mixed system containing the alkalized dextrin and monochloroacetic acid in a mass ratio of 1:0.3-1 at 40-45° C. for 4-6 h under the pH of 6.5-7.5 to obtain a homogeneous carboxymethyl dextrin with a substitution degree of 0.3-0.7.

In some embodiments, a method for preparing the dextrin with a homogeneous polymerization degree comprises:

rice starch is dispersed into a phosphate buffer solution with the pH of 5-6, heated to be gelatinized and cooled to 50-55° C., then pullulanase with the addition amount of 50-100 U/g rice starch is added to perform debranching treatment for 20-24 h. The obtained product is subjected to water bath treatment at 30-60° C., then graded using an ethanol stepwise precipitation method to obtain the dextrin with a homogeneous polymerization degree of 60-80.

In some more specific embodiments, the carboxymethyl dextrin can be prepared by the following method:

10 g of rice starch is dispersed into 200 mL of phosphate buffer with the pH of 5.5, heated to be gelatinized for 1 h and then cooled to 50-55° C., then pullulanase with the addition amount of 50 U/g rice starch is added to perform debranching treatment at 20-50° C. for 20-24 h. The obtained product is subjected to water bath treatment at 30-60° C., and then the product obtained after water bath treatment is graded using the ethanol stepwise precipitation method to obtain the dextrin with the homogenous polymerization degree;

the dextrin with the homogenous polymerization degree is alkalized at 35-40° C. for 3-5 h, and then the reaction system containing dextrin and monochloroacetic acid in a feed ratio of 1:0.3-1 is etherified with the pH of 6.5-7.5 at 40-45° C. for 4-6 h to obtain homogenous carboxymethyl dextrin with a high substitution degree, and the obtained carboxymethyl dextrin is dried and stored in a drier.

In the present application, the polypeptide EHT and quercetin are simply dissolved and compounded at the pH of 12, and NaCl is added to adjust the ionic strength of the mixed system to promote the self-assembling of the polypeptide, then the pH of the mixed system is adjusted to 9, then the obtained composite and anthocyanin are covalently grafted under the alkaline condition, and the pH of the reaction system is adjusted to 3, then the grafted composite particle is compounded with carboxymethyl dextrin through electrostatic interaction to form a starch-based double-loaded functional nanoparticle with a core-shell structure. The whole process does not involve organic solvents, chemical treatments or complicated processes and equipment. Furthermore, in the present application, the loading of biologically active components of two different polar components is realized in the composite system by using a double loaded technology, and components with different molecular properties can be distributed in various regions of the core-shell system of the composite particle to form a hierarchical structure, which has protection and release effects on each active component and can enhance the biological stability between components. And meanwhile, a synergistic effect can be generated by compounding different biological active compounds, so as to achieve the purpose of promoting health more effectively.

In a more specific embodiment of the present application, a starch-based double-loaded functional nanoparticle is realized based on a pH-driven method, comprising the following steps:

(1) restrictive hydrolysis treatment is performed on egg high-density lipoprotein by using any one or more of trypsin, alkaline protease and neutral protease to form the polypeptide EHT with a specific molecular weight, wherein the temperature of the hydrolysis (enzymatic hydrolysis) reaction is 37° C., the time of the hydrolysis treatment is 0.5-4.5 h (preferably 3.5 h), the pH of the enzymatic hydrolysis reaction system is 8.0-9.0 (preferably 8.0), and then the hydrolyzed product is dialyzed at 0-4° C. for 48 h. The specification of the used cellulose dialysis bag is 5000 Daltons. The obtained hydrolysate is mixed with ethanol followed by a centrifugation to remove the precipitate, and the supernatant is subjected to freeze drying and then treated in an oven at 80° C. for 10 min; the obtained egg high-density lipoprotein hydrolysate (i.e., EHT) has a hydrolysis degree of 6.7%-10% and a molecular weight of 5-20 kDa;

(2) EHT and quercetin powder are dispersed into water, and NaCl is added to adjust the ionic strength of the mixed system to 80-120 mmol/L; the concentration of EHT is 10-50 mg/mL (preferably 20 mg/mL), the mass ratio of quercetin powder to EHT is 1:100-1:10 (preferably 1:10), and the pH of the mixed system is adjusted to 10.0-12.0 (preferably, pH is 12) by using a NaOH solution. Under these conditions, self-assembling is performed by continuously stirring to form a quercetin-polypeptide micelle nanoparticle;

(3) the solution of the quercetin-polypeptide micelle nanoparticle and the anthocyanin solution are mixed and continuously stirred in the alkaline environment with the pH value of 9.0-9.5 (preferably, pH is 9.0) to perform covalent grafting reaction for 20-30 h (preferably 24 h), so as to form a quercetin-polypeptide-anthocyanin graft in which the mass ratio of quercetin and anthocyanin is 1:2-2:1 (preferably 1:1), and then the pH of the obtained mixed solution is adjusted to 7 by stirring the mixed solution while dropwise adding HCl solution. The obtained reaction mixture is then dialyzed for 20-24 h after the modification treatment is completed, and the cutoff molecular weight of the dialysis bag is 3500-4000 Daltons;

(4) the carboxymethyl dextrin is compounded with the quercetin-polypeptide-anthocyanin graft through electrostatic interaction to obtain the starch-based double-loaded functional nanoparticle. Specifically, the solution of the quercetin-polypeptide-anthocyanin graft is mixed with the carboxymethyl dextrin solution, and the pH of the mixed solution is adjusted to 3 by stirring while dropwise adding the HCl solution so that the quercetin-polypeptide-anthocyanin graft is compounded with carboxymethyl dextrin, wherein the mass ratio of polypeptide to carboxymethyl dextrin is 4:1-1:4 (preferably 1:1).

Further, in step (1), the concentration of the egg high-density lipoprotein in the hydrolysis reaction system is 5 wt %. The added amounts of the trypsin, alkaline protease and neutral protease are 20-100 U/g egg high-density lipoprotein, preferably 50 U/g egg high-density lipoprotein.

Further, the continuous stirring in step (2) means stirring at the speed of 300-600 rpm for 30-60 min, preferably stirring at the speed of 500 rpm for 30 min.

Further, the stirring speed used in step (3) is 300-600 rpm, preferably 300 rpm.

Further, step (4) also comprises:

I. the rice starch is dispersed into a phosphate buffer solution with the pH of 5-6 to form a rice starch dispersion having a mass percentage concentration of about 5%, heated to be gelatinized for 1 h and then cooled to 50-55° C., then pullulanase is added to perform debranching treatment for 20-24 h. The obtained product is subjected to water bath treatment and graded by using an ethanol stepwise precipitation method (ethanol:water=1:2-2:1, a volume ratio) to obtain dextrin with homogenous polymerization degree; preferably, the pH of the phosphate buffer solution is 5.5; preferably, the addition amount of pullulanase is 50-100 U/g rice starch, more preferably 50 U/g rice starch; preferably, the polymerization degree of the dextrin is 60-80, more preferably 65-80; and II. the dextrin with homogenous polymerization degree is alkalized at 35~40° C. (preferably 40° C.) for 3-5 h, wherein the addition amount of NaOH is preferably 0.6 g/g dextrin, and the reaction time is preferably 4 h, and then the mixed system containing the dextrin and monochloroacetic acid in a feed ratio of 1:0.3-1 (preferably, 1:0.6) is etherified at 40~45° C. with the pH of 6.5-7.5 for 4-6 h (preferably, 4 h) to obtain homogenous carboxymethyl dextrin (CMD) with a high substitution degree; preferably, the substitution degree of monochloroacetic acid in the CMD is 0.3-0.7.

Another aspect of the embodiment of the present application provides the starch-based double-loaded functional colloid nanoparticle prepared by the method. The starch-based double-loaded functional colloid nanoparticle has a nanoparticle size, which is easy to be transported and absorbed, and can improve the absorption efficiency of hydrophobic biological active substances, with the advantages of high antioxidant activity, stability against environmental stress (pH and ionic strength) and the like.

Further, the starch-based double-loaded functional colloid nanoparticle is spherical, with the core-shell structure, and possesses a particle size of 189-259 nm as well as an absolute $\zeta$ potential value of 26.1-35.2 mV.

Further, in the starch-based double-loaded functional colloid nanoparticle, the encapsulation efficiency of quercetin can reach 95.83%, and that of anthocyanin can be as high as 90.95%.

Another aspect of the embodiment of the present application provides application of the starch-based double-loaded functional colloid nanoparticle in the preparation of an antioxidant delivery system or foods.

The present application will be described in further detail below with reference to the embodiments, but the embodiments of the present application are not limited thereto. Unless otherwise specified, the raw materials are all commercially available products. The test methods are all conventional methods.

The egg high-density lipoproteins used in the following examples are mainly obtained by the following methods:

Fresh eggs are broken, and the yolks are rolled on filter paper to remove egg white protein after egg whites are isolated from yolks, Vitelline membranes are disrupted with a razor blade, and yolks are pooled in a beaker. Then, an equal volume of sodium chloride solution (0.17 M) is then added to the yolks, and the mixture is stirred for 1 h, followed by centrifugation at 10,000 g at 4° C. for 45 min to obtain the supernatant and precipitate. The precipitate is washed 3 times with 0.17 M NaCl solution. The washed precipitate paste is re-dissolved into 0.2 M NaCl solution, then stirred by adding ammonium sulfate solution (15%, w/v), and then centrifuged at 10,000 g at 4° C. for 15 min after being precipitated for 30 min. The supernatant is dialyzed against distilled water overnight using an 8 kDa cutoff membrane, with hourly changes of distilled water for the first four hours to eliminate sodium chloride and ammonium sulfate. Then, the desalted solution is then centrifuged at 10,000 g for 30 min at 4° C. The precipitate after centrifugation is rich in egg high-density lipoprotein. The egg high-density lipoprotein is subjected to freeze drying using a freeze dryer and stored in a drier.

Encapsulation efficiency of quercetin (%)=(quercetin content in supernatant after centrifugation/total quercetin content)×100.

Encapsulation efficiency of anthocyanin (%)=(anthocyanin content in supernatant after centrifugation/total anthocyanin content)×100.

The technical solutions of the present application will be described in further detail below through several embodiments and accompanying drawings. However, the selected embodiments are only intended to illustrate the present application and do not limit the scope of the present application.

Example 1. A preparation method of a starch-based double-loaded functional nanoparticle comprises the following steps:

(1) Preparation of egg high-density polypeptide EHT 1 g of egg high-density lipoprotein was accurately weighed and dispersed into 20 mL deionized water, and the pH of the solution was adjusted to 8.0, the solution was heated in a water bath pot of 37° C. until the temperature was constant. Trypsin (50 U/g egg high-density lipoprotein) was added and uniformly stirred; the resulting mixed solution was hydrolyzed for a certain time in a constant-temperature water bath of 37° C., the hydrolysate was dialyzed at 0-4° C. for 48 h, and the specification of the used cellulose dialysis bag was about 5000 Daltons, the obtained hydrolysate was mixed with ethanol so that the final concentration of ethanol was 20%, the above mixture was centrifuged at 4000 g for 20 min to remove the precipitate, the supernatant was subjected to freeze drying, and the lyophilized polypeptide was treated in an 80° C. oven for 10 min.

Figure 1A:
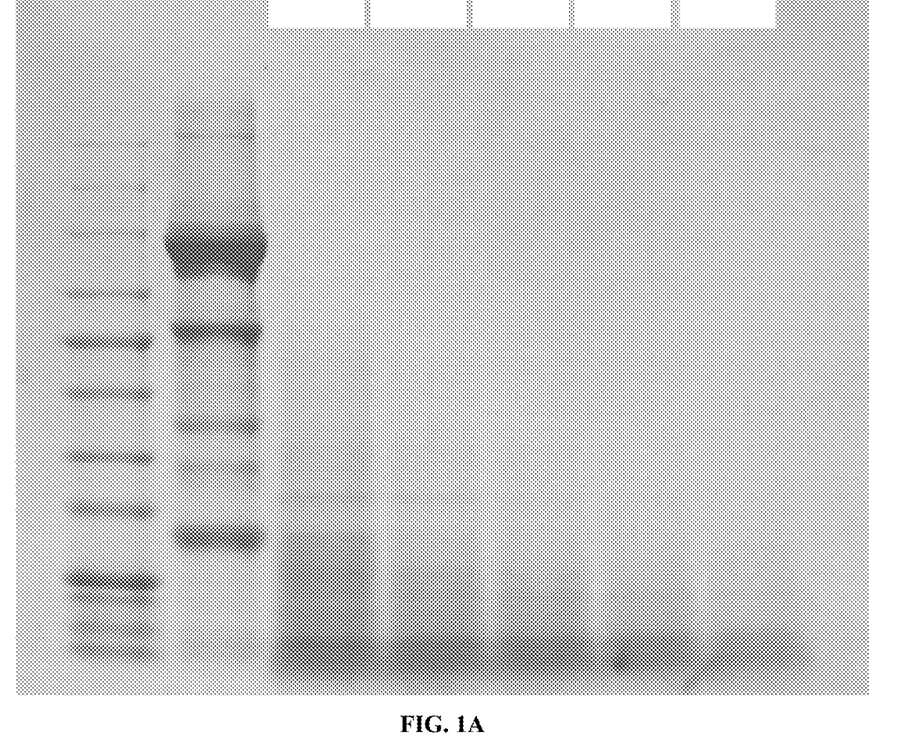
FIG. 1A is an SDS-PAGE test image of an egg high-density lipoprotein and polypeptide (EHT) in example 1.
Figure 1B:
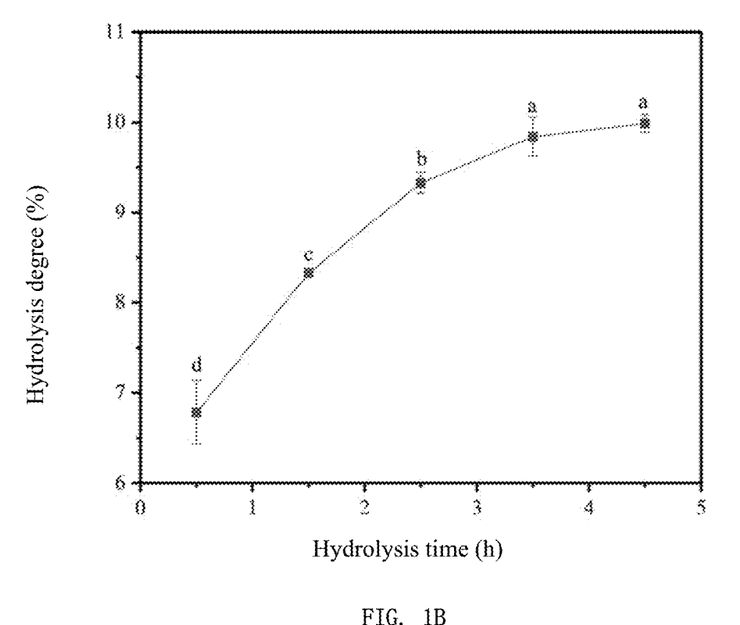
FIG. 1B is a diagram showing a relationship between hydrolysis degree and hydrolysis time of an egg high-density lipoprotein in example 1.

Referring to FIGS. 1A and 1B, lanes 1-7 respectively represent molecular weight distributions of protein Marker, high-density lipoprotein (HDL) and hydrolysates treated with trypsin for 0.5 h (trypsin 0.5), 1.5 h (trypsin 1.5), 2.5 h (trypsin 2.5), 3.5 h (trypsin 3.5) and 4.5 h (trypsin 4.5). With the increase of hydrolysis time, the molecular weight of EHT is gradually decreased and the hydrolysis degree is gradually increased.

Figure 2A:
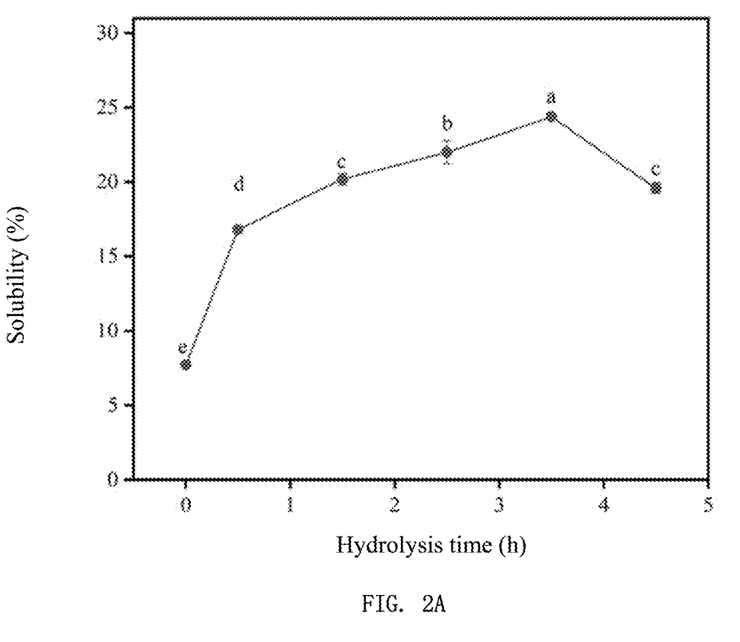
FIG. 2A is a test graph of a solubility of polypeptide EHT at the pH of 7 in example 1.
Figure 2B:
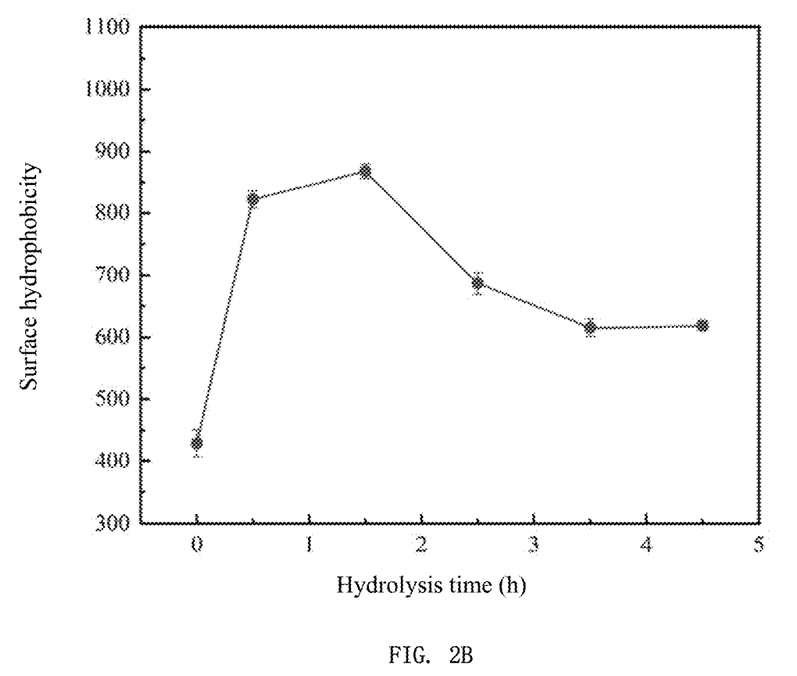
FIG. 2B is a test graph of surface hydrophobicity of polypeptide EHT at the pH of 7 in example 1.

Referring again to FIGS. 2A and 2B, the solubility of EHT with different hydrolysis times at pH 7 is shown respectively. It can be seen from FIG. 2A that the solubility of EHT in this example is significantly increased compared with that of egg HDL, and it is increased first and then decreased with the increase of hydrolysis time, reaching the maximum value after hydrolysis for 3.5 h. It can be seen in FIG. 2B that the surface hydrophobicity of EHT in this example is remarkably increased compared with that of egg HDL, and it is increased first and then decreased with the increase of hydrolysis time, reaching the maximum value after hydrolysis for 1.5 h. Through hydrolysis via Trypsin, the egg HDL is reduced in molecular weight and loose in structure, leading to reduction in intermolecular forces and improvement in its solubility. Due to the exposure of internal hydrophobic groups, the surface hydrophobicity is increased significantly.

Figure 3A:
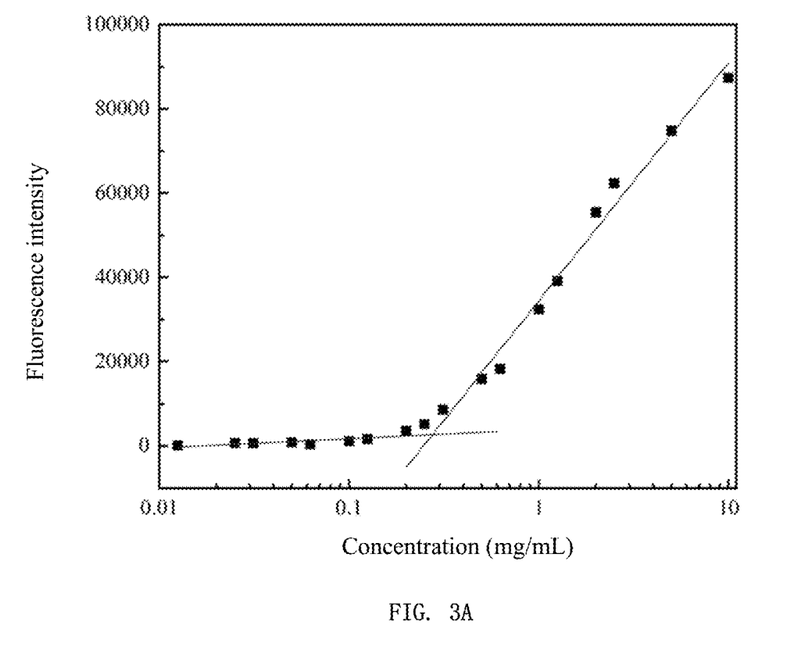
FIG. 3A is a test graph of a critical micelle concentration of a polypeptide EHT at the pH of 7 in example 1.
Figure 3B:
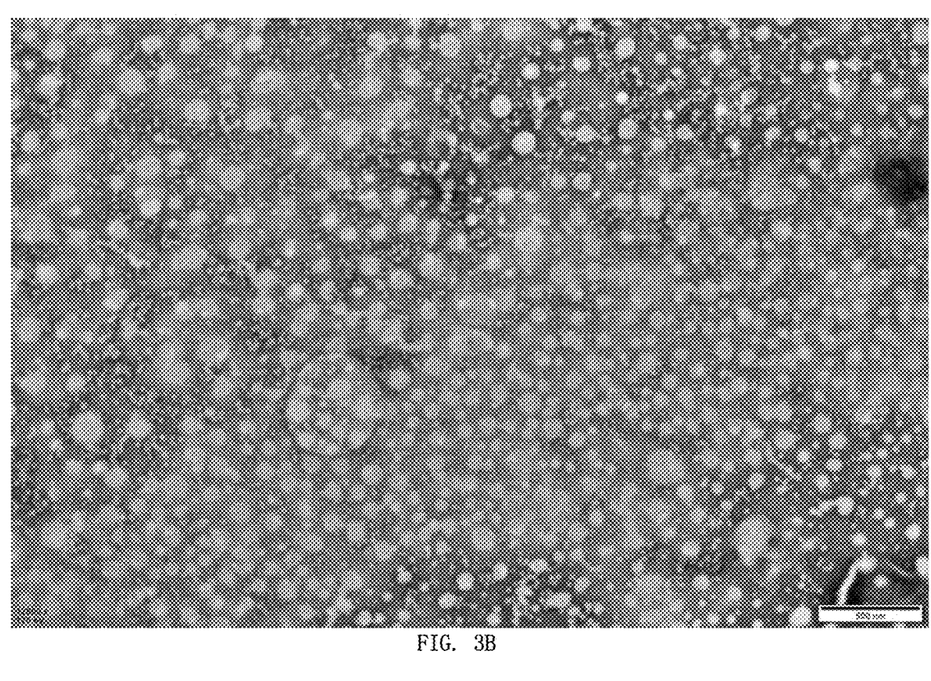
FIG. 3B is a transmission electron microscope (TEM) image of polypeptide EHT at the pH of 7 in example 1

Referring to FIG. 3A, a relationship curve of fluorescence intensities of EHT after being hydrolyzed for 3.5 h via Trypsin under difference concentrations is shown. When the concentration is higher than 0.3 mg/ml, EHT is subjected to self-assembling to form a spherical micelle nanoparticle. FIG. 3B is a TEM image of EHT after being hydrolyzed for 3.5 h via Trypsin at the pH of 7. Therefore, it is further proved that EHT can be self-assembled to form the spherical micelle nanoparticle.

(2) Preparation of quercetin-polypeptide-anthocyanin graft

Quercetin powder and EHT were dispersed into water in a mass ratio of 1:50 so that the concentration of EHT was 50 mg/ml, NaCl was added to adjust the ionic strength of the system to 100 mmol/L, then the pH was adjusted to 12, and the system was stirred and mixed for 30 min. A certain mass of anthocyanin powder was added into the above mixed solution so that the mass ratio of quercetin to anthocyanin was 1:2. The pH of the solution was adjusted to 9.0, and the mixed solution was stirred at the rotation speed of 500 rpm for 24 h; the pH of the mixed solution was adjusted to 7 using 1 M HCl solution. After the modification treatment was completed, the reaction system was dialyzed for about 24 h, and the cutoff molecular weight of the dialysis bag is 3500-4000 Daltons.

(3) preparation of carboxymethyl dextrin: 10 g of rice starch was dispersed into 200 mL of phosphate buffer solution with the pH of 5.5, heated to be gelatinized for 1 h and then cooled to about 50° C., then pullulanase with the addition amount of 50 U/g rice starch was added to perform debranching treatment for about 24 h, the obtained product was subjected to water bath treatment at 60° C., and graded by using an ethanol stepwise precipitation method to obtain dextrin with homogenous polymerization degree, wherein a volume ratio of ethanol to water was 1:1. The dextrin with the homogenous polymerization degree was alkalized at about 35° C. for 3 h, then a feed ratio of dextrin to monochloroacetic acid was 1:0.6 at the pH of 7.5, the mixed system was etherified at 40° C. for 4 h to obtain homogenous carboxymethyl dextrin with high substitution degree, and the obtained carboxymethyl dextrin was dried and stored in a dryer.

(4) The solution system containing quercetin-polypeptide-anthocyanin graft was mixed with the carboxymethyl dextrin solution, wherein the mass ratio of polypeptide to carboxymethyl dextrin was 4:1-1:4. The pH of the above mixed solution was adjusted to 3 by stirring while dropwise adding the HCl solution, and the starch-based double-loaded functional colloid nanoparticle with the core-shell structure was obtained after freeze drying.

Figure 4:
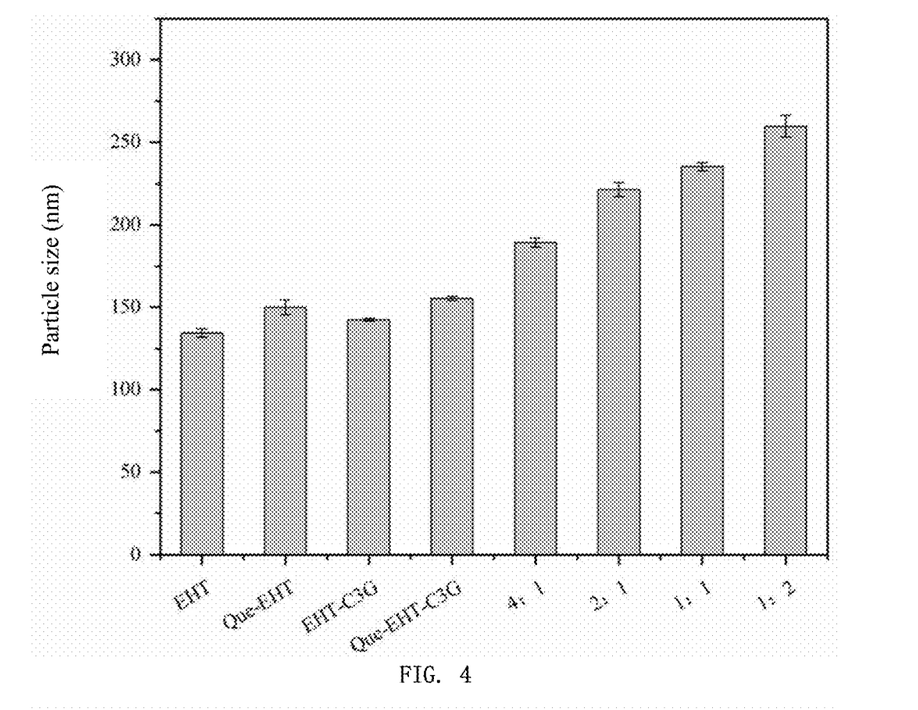
FIG. 4 is a particle size change graph of starch-based double-loaded functional nanoparticles obtained when different addition ratios of carboxymethyl dextrin are adopted in example 1.

Referring to FIG. 4, it shows the particle sizes of starch-based double-loaded functional colloid nanoparticles formed by EHT and complexes with different EHT: carboxymethyl dextrin mass ratios. It can be seen from FIG. 4 that after quercetin is added, the particle size of quercetin composite nanoparticle is increased, which proves that quercetin is successfully loaded by EHT. After covalent grafting with anthocyanin, the particle size of quercetin-polypeptide-anthocyanin graft is slightly increased. With the increase of the addition proportion of carboxymethyl dextrin, the particle size of the starch-based double-loaded functional colloid nanoparticle is significantly increased.

Figure 5:
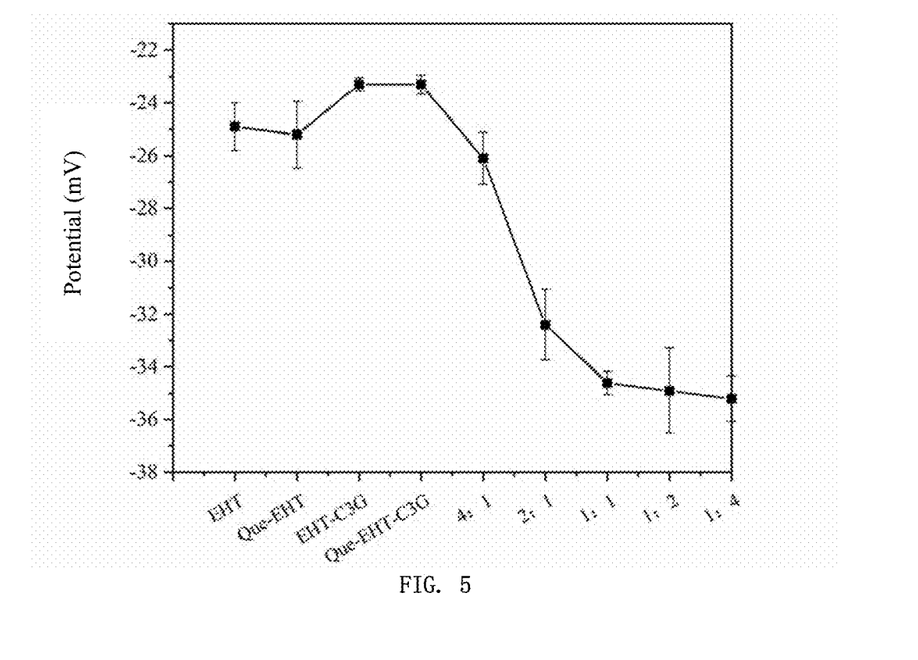
FIG. 5 is a potential change graph of starch-based double-loaded functional nanoparticles obtained when different addition ratios of carboxymethyl dextrin are adopted in example 1.

Referring to FIG. 5, it shows the potentials of the starch-based double-loaded functional colloid nanoparticles formed by EHT and complexes with different EHT: carboxymethyl dextrin mass ratios. It can be seen from FIG. 5 that after the addition of quercetin, the potential of the quercetin composite nanoparticle has no obvious change, which may be attributed to the fact that quercetin is encapsulated in the internal hydrophobic region of the spherical micelle nanoparticle formed by self-assembling of EHT. After covalent grafting with anthocyanin, the potential of the quercetin-polypeptide-anthocyanin graft is slightly increased. With the increase of the addition proportion of carboxymethyl dextrin, the carboxymethyl dextrin with more negative charges is adsorbed on the surface of the particle, and the potential of the starch-based double-loaded functional colloid nanoparticle is significantly increased.

Figure 6:
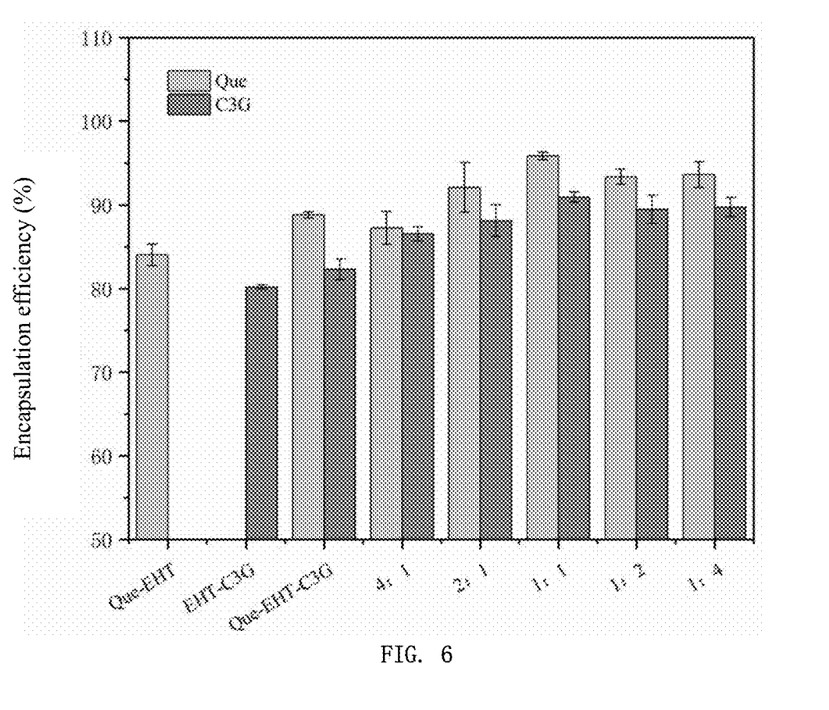
FIG. 6 is a change graph of load efficiencies of a starch-based double-loaded functional nanoparticle in example 1 on quercetin and anthocyanin.

Referring to FIG. 6, it shows the change in support efficiencies of the starch-based double-loaded functional colloid nanoparticle in this example on quercetin and anthocyanin. It can be seen from FIG. 6 that when quercetin and anthocyanin are simultaneously embedded, the encapsulation efficiency is increased. After different proportions of carboxymethyl dextrin are added, the encapsulation efficiency is further increased, and the maximum encapsulation efficiency is obtained when the mass ratio of EHT to carboxymethyl dextrin is 1:1.

Figure 7:
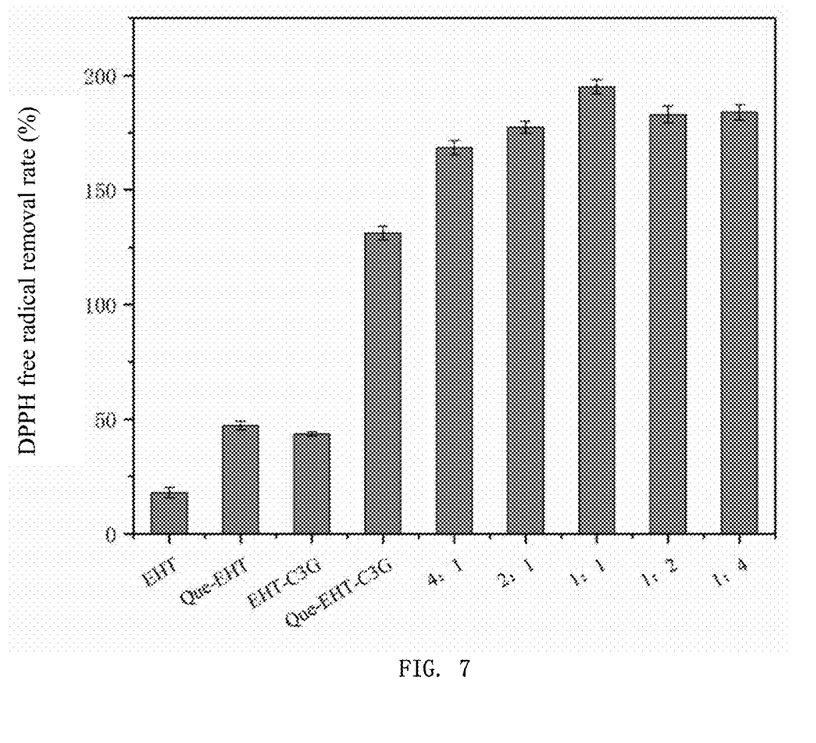
FIG. 7 is a change test graph of DPPH free radical removal rates of quercetin and anthocyanin in a starch-based double-loaded functional nanoparticle in example 1.

Referring to FIG. 7, it shows the change in DPPH free radical removal rates of quercetin and anthocyanin of starch-based double-loaded functional colloid nanoparticle in this example. It can be seen from FIG. 7 that EHT has a low DPPH free radical removal rate and low antioxidant activity. After quercetin and anthocyanin are encapsulated, the DPPH radical removal rate is significantly increased. After different proportions of carboxymethyl dextrin are added, the contents of the encapsulated quercetin and anthocyanin are increased due to further improvement of encapsulation efficiency, performing higher antioxidant activity.

Figure 8:
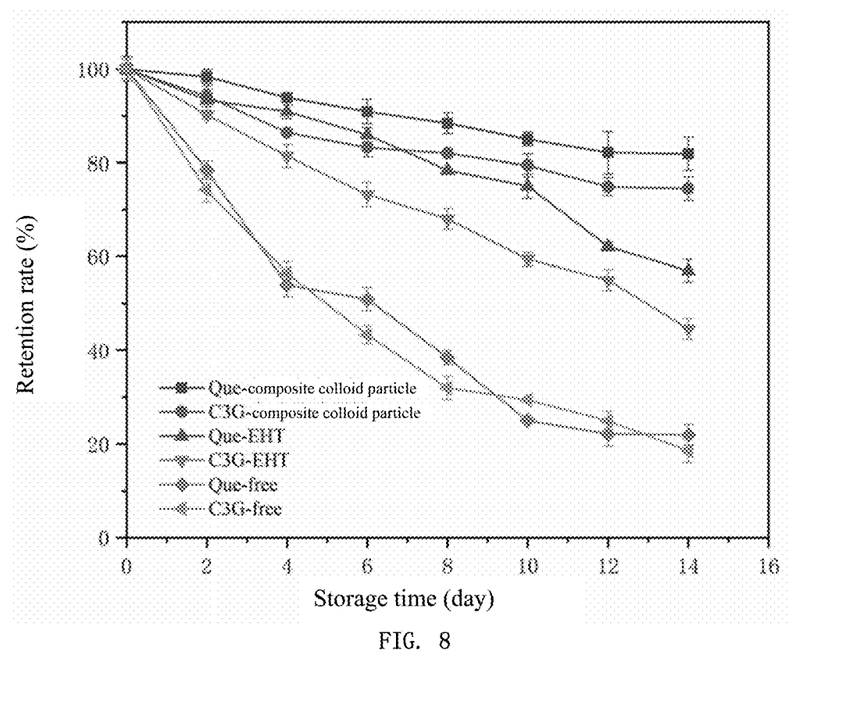
FIG. 8 is a retention rate change test graph of quercetin and anthocyanin in a starch-based double-loaded functional nanoparticle in example 1 during the storage for 14 days.

Referring to FIG. 8, it shows the changes in the retention rates of quercetin and anthocyanin of the starch-based double-loaded functional colloid nanoparticle (a mass ratio of EHT:carboxymethyl dextrin is 1:1) in this example during the storage for 14 days. It can be seen from FIG. 8 that quercetin and anthocyanin alone are easy to degrade in the environment, and only about 20% of quercetin and anthocyanin can be retained after being stored for 14 days. After quercetin and anthocyanin are embedded in EHT, the retention rates are increased significantly reaching 56.9% and 44.5%, respectively. After quercetin and anthocyanin are embedded in the starch-based double-loaded functional colloid nanoparticle (a mass ratio of EHT:carboxymethyl dextrin is 1:1), the retention rates are increased significantly, reaching 81.9% and 74.9%, respectively. The significant increase of retention rate proves that the starch-based double-loaded functional colloid nanoparticle can effectively protect quercetin and anthocyanin from being degraded.

Example 2. A preparation method of a starch-based double-loaded functional nanoparticle comprises:

(1) Preparation of egg high-density polypeptide EHT 1 g of eggs high-density lipoprotein was accurately weighed and dispersed into 20 mL deionized water, and the pH of the solution was adjusted to 8.0, the solution was heated in a water bath pot of 37° C. until the temperature was constant. A certain neutral protease (20 U/g egg high-density lipoprotein) was added and uniformly stirred; the resulting mixed solution was hydrolyzed for 3.5 h in a constant-temperature water bath of 37° C., the hydrolysate was dialyzed at 0-4° C. for 48 h, and the specification of the used cellulose dialysis bag was about 5000 Daltons, the obtained hydrolysate was mixed with ethanol so that the final concentration of ethanol was 10%, the above mixture was centrifuged at 4000 g for 20 min to remove the precipitate, the supernatant was subjected to freeze drying, and the lyophilized polypeptide was treated in an 80° C. oven for 10 min.

(2) Preparation of quercetin-polypeptide-anthocyanin graft

Quercetin powder and EHT were dispersed into water in a mass ratio of 1:20 so that the concentration of EHT was 50 mg/ml, NaCl was added to adjust the ionic strength of the system to 80 mmol/L, then the pH was adjusted to 12, and the system was stirred and mixed for 30 min. A certain mass of anthocyanin powder was added into the above mixed solution so that the mass ratio of quercetin to anthocyanin was 1:1. The pH of the solution was adjusted to 9.0, and the mixed solution was stirred at the rotation speed of 500 rpm for 24 h; the pH of the mixed solution was adjusted to 7 using 1 M HCl solution. After the modification treatment was completed, the reaction system was dialyzed for 20-24 h.

(3) preparation of carboxymethyl dextrin: 10 g of rice starch was dispersed into 200 mL of phosphate buffer solution with the pH of 5.5, heated to be gelatinized for 1 h and then cooled to about 55° C., then pullulanase with the addition amount of 50 U/g rice starch was added to perform debranching treatment for 20-24 h, the obtained product was subjected to water bath treatment at 60° C., and then the product obtained after water bath treatment was graded by using an ethanol stepwise precipitation method to obtain dextrin with homogenous polymerization degree, wherein a volume ratio of ethanol to water was 2:1. The dextrin with the homogenous polymerization degree was alkalized at about 40° C. for 5 h, then a feed ratio of dextrin to monochloroacetic acid was 1:0.5 at the pH of 7.5, the mixed system was etherified at 45° C. for 5 h to obtain homogenous carboxymethyl dextrin with high substitution degree, and the obtained carboxymethyl dextrin was dried and stored in a dryer.

(4) The solution system containing quercetin-polypeptide-anthocyanin graft was mixed with the carboxymethyl dextrin solution, wherein the mass ratio of polypeptide to carboxymethyl dextrin was 1:1. The pH of the above mixed solution was adjusted to 3 by stirring while dropwise adding HCl solution, and the starch-based double-loaded functional colloid nanoparticle with the core-shell structure was obtained after freeze drying.

Example 3. A preparation method of a starch-based double-loaded functional nanoparticle comprises:

(1) Preparation of egg high-density polypeptide EHT 1 g of eggs high-density lipoprotein was accurately weighed and dispersed into 20 mL deionized water, and the pH of the solution was adjusted to 8.0, the solution was heated in a water bath pot of 37° C. until the temperature was constant. A certain alkaline protease (100 U/g egg high-density lipoprotein) was added and uniformly stirred; the resulting mixed solution was hydrolyzed for 2.5 h in a constant-temperature water bath of 37° C., the hydrolysate was dialyzed at 0-4° C. for 48 h, and the specification of the used cellulose dialysis bag was about 5000 Daltons, the obtained hydrolysate was mixed with ethanol so that the final concentration of ethanol was 25%, the above mixture was centrifuged at 4000 g for 20 min to remove the precipitate, the supernatant was subjected to freeze drying, and the lyophilized polypeptide was treated in an 80° C. oven for 10 min.

(2) Preparation of quercetin-polypeptide-anthocyanin graft

Quercetin powder and EHT were dispersed into water in a mass ratio of 1:10 so that the concentration of EHT was 20 mg/ml, NaCl was added to adjust the ionic strength of the system to 120 mmol/L, then the pH was adjusted to 12, and the system was stirred and mixed for 30 min. A certain mass of anthocyanin powder was added into the above mixed solution so that the mass ratio of quercetin to anthocyanin was 1:1. The pH of the solution was adjusted to 9.0, and the mixed solution was stirred at the rotation speed of 500 rpm for 30 h; the pH of the mixed solution was adjusted to 7 using 1 M HCl solution. After the modification treatment was completed, the reaction system was dialyzed for 24 h.

(3) preparation of carboxymethyl dextrin: 10 g of rice starch was dispersed into 200 mL of phosphate buffer solution with the pH of 5.5, heated to be gelatinized for 1 h and then cooled to about 52° C., then pullulanase with the addition amount of 100 U/g rice starch was added to perform debranching treatment for 20 h, the obtained product was subjected to water bath treatment at 60° C., and then the product obtained after water bath treatment was graded by using an ethanol stepwise precipitation method to obtain dextrin with homogenous polymerization degree, wherein a volume ratio of ethanol to water was 1:1. The dextrin with the homogenous polymerization degree was alkalized at about 38° C. for 5 h, then a feed ratio of dextrin to monochloroacetic acid was 1:0.6 at the pH of 7, the mixed system was etherified at 45° C. for 6 h to obtain homogenous carboxymethyl dextrin with high substitution degree, and the obtained carboxymethyl dextrin was dried and stored in a dryer.

(4) The solution system containing quercetin-polypeptide-anthocyanin graft was mixed with the carboxymethyl dextrin solution, wherein the mass ratio of polypeptide to carboxymethyl dextrin was 1:1. The pH of the above mixed solution was adjusted to 3 by stirring while dropwise adding HCl solution, and the starch-based double-loaded functional colloid nanoparticle with the core-shell structure was obtained after freeze drying.

Comparative example 1: the preparation method of the starch-based double-loaded functional colloid nanoparticle provided in comparative example 1 is basically the same as that in example 1 (a mass ratio of polypeptide to carboxymethyl dextrin is 1:1), and the difference is that the addition amount of trypsin in step (1) is 10 U/g egg high-density lipoprotein.

There are basically no stable starch-based double-loaded functional colloid nanoparticles in this comparative example for the following reasons: the obtained polypeptide has insufficient hydrolysis degree and high protein molecular weight, the dense core structure still exists, insufficient exposure of internal hydrophobic groups are insufficient to expose so that polypeptide cannot achieve hydrophilic-lipophilic balance and cannot be effectively self-assembled into micelle nanoparticles, and then the encapsulation efficiency of the hydrophobic bioactive component quercetin is significantly reduced.

Comparative example 2: the preparation method of a starch-based double-loaded functional colloid nanoparticle provided in comparative example 1 is basically the same as that in example 2 (a mass ratio of polypeptide to carboxymethyl dextrin is 1:1), and the difference is that the addition amount of trypsin in step (1) is 150 U/g egg high-density lipoprotein.

There is basically no stable starch-based double-loaded functional colloid nanoparticles in this comparative example for the following reasons: the hydrolysis degree of the obtained polypeptide is too high, a large amount of polypeptides with small molecular weights is generated, and the internal hydrophobic groups are exposed. Polypeptides with small molecular weights are re-aggregated due to strong hydrophobic interaction, which causes hydrophobic groups to be reburied inside the aggregate. Furthermore, the solubility is reduced, which is not conducive to realizing the hydrophilic-lipophilic balance of polypeptides and then creating a negative impact on their ability to perform self-assembling to form the micelle nanoparticles. The encapsulation efficiency of quercetin is significantly reduced, which is not conducive to the formation of double-loaded functional starch-based colloid nanoparticles. The re-aggregation of small molecular polypeptides causes the charged groups to be partially buried, which is also not conducive to the compounding of carboxymethyl dextrin with quercetin polypeptide anthocyanin graft through electrostatic interaction. The side chain of polysaccharide cannot be effectively used to provide steric hindrance for starch-based colloid nanoparticles, which is not conducive to the stability of starch-based colloid nanoparticles.

Comparative example 3: the preparation method of a starch-based colloid nanoparticle provided in comparative example 3 is basically the same as that in example 1, and the difference is that:

step (2) comprises: EHT was dispersed into water so that the concentration of egg EHT was 20 mg/mL, the pH was adjusted to 12, the solution was stirred for 30 min, and then anthocyanin powder was added so that a mass ratio of anthocyanin to egg EHT was 1:1. The pH of the solution was adjusted to 9.0 and the solution was stirred to react at the rotation speed of 500 rpm for 30 h; the pH of the mixed solution was adjusted to 7 with 1 M HCl solution, and then the reaction system was dialyzed for 24 h.

The particle size of the product obtained by this comparative example is significantly reduced compared with that of the corresponding product in example 1, and the DPPH free radical removal rate is also significantly reduced.

Comparative example 4: the preparation method of the starch-based colloid nanoparticles provided in comparative example 4 is basically the same as that in example 1, and the difference is that:

step (2) comprises: quercetin powders and egg EHT were dispersed into water in a mass ratio of 1:10 so that the concentration of egg EHT was 20 mg/mL, the pH was adjusted to 12, the solution was stirred for 30 min, and then the obtained product was directly applied to step (4).

The particle size of the product obtained by this comparative example is significantly reduced compared with that of the corresponding product in example 1, and the oxidation resistance is also significantly reduced, the stability (especially thermal stability) against environmental stress is also significantly reduced.

Comparative example 5: the preparation method of a starch-based double-loaded functional colloid nanoparticle provided in comparative example 5 is basically the same as that in example 1. The difference is that step (3) is omitted, and commercially available carboxymethyl-β-cyclodextrin is used to replace the carboxymethyl dextrin in step (4), wherein a mass ratio of quercetin-egg polypeptide-anthocyanin graft to carboxymethyl dextrin is 1:1.

There is basically no stable starch-based double-loaded functional colloid nanoparticles in this comparative example for the following reasons: the commercially available carboxymethyl-β-cyclodextrin is formed by 7 D-glucose units through α-1, 4 glycosidic bonds, and β-CD has a special cone cavity structure with a wide upper part and a narrow lower part. The secondary hydroxyl groups at positions C-2 and C-3 are located at the wide end of the cavity, and the non-polar hydrogen and ether oxygen radicals at positions C-3 and C-5 are located inside the ring molecule. The hydroxyl groups with hydrophilicity on the surface and internal hydrophobicity groups make the external of the molecule is hydrophilic and the internal of the molecule is hydrophobic. But the solubility of β-CD in the solution with low pH is low, and the compounding efficiency with quercetin-polypeptide-anthocyanin graft is low.

In addition, the inventor of this case also conducted tests with other raw materials, process operations and process conditions described in this specification with reference to the above embodiments, and achieved ideal results.

In the above embodiments of the present application, the molecular weight distribution, hydrolysis degree, solubility and surface hydrophobicity of the egg high-density lipoprotein polypeptide are evaluated, the particle sizes and potentials of the polypeptide and the composite nanoparticle are measured by a zeta potentiometer. According to the present application, the composite nanoparticles are prepared under the condition that the mass ratio of polypeptide to carboxymethyl dextrin is 4:1-1:4. Since the egg high-density lipoprotein polypeptide binds to quercetin through hydrophobic interaction, anthocyanin can react with the amino and sulfhydryl side chain of the polypeptide to form C—N and C—S bonds, and the reaction product maintain the antioxidant activity of polyphenol to a great extent. In the acidic environment, the negatively charged carboxymethyl dextrin molecule can be compounded with the positively charged quercetin polypeptide anthocyanin graft through electrostatic interaction to form a composite particle with a core-shell structure. The external carboxymethyl dextrin layer can enhance the rigidity of the nanoparticle, and the polysaccharide side chain can provide a greater steric hindrance for the composite particle.

In the preparation method of starch-based double-loaded functional nanoparticles of the present application, raw materials derived from natural sources are used, and self-assembled colloid nanoparticle with good properties can be obtained by adjusting pH without using any organic reagents. The method is simple, efficient, safe, and easy to produce. The obtained product has a nanoparticle size, embeds two biological active substances with different polarities, performing the advantages of high antioxidant activity, stability against environmental stress (pH and ionic strength) and the like. It allows efficient delivery, and is widely applied to the fields of delivery of nutrients, stabilization of biologically active substances and the like.

Although the present application has been described with reference to illustrative embodiments, those skilled in the art will understand that various other changes, omissions and/or additions may be made without departing from the spirit and scope of the present application, and the elements of the embodiments may be replaced with substantial equivalents. In addition, many modifications may be made without departing from the scope of the present application to adapt specific situations or materials to the teachings of the present application. Therefore, it is not intended to limit the present application to the specific embodiments disclosed for executing the present application, but to make the present application include all embodiments within the scope of the appended claims.

What is claimed is:

1. A preparation method of a starch-based double-loaded functional nanoparticle, comprising:
   1) performing a restrictive hydrolysis treatment on egg high-density lipoprotein by using proteases, and then isolating and purifying by using dialysis and ethanol precipitation methods to obtain a polypeptide;
   2) performing self-assembling on a first mixed system containing the polypeptide and quercetin under a first alkaline condition to form a micelle nanoparticle;
   3) performing a covalent grafting reaction on a second mixed system containing the micelle nanoparticle and anthocyanin in a second alkaline environment to form a graft; and
   4) Electrostatically compounding carboxymethyl dextrin with the graft to obtain the starch-based double-loaded functional nanoparticle.

2. The preparation method according to claim 1, wherein in step 1, a temperature of the restrictive hydrolysis treatment is 30-55° C., a time of the restrictive hydrolysis treatment is 0.5-4.5 h, and a pH of a restrictive hydrolysis system is 8.0-9.0, and an addition amount of the protease is 20-100 U/g of the egg high-density lipoprotein.

3. The preparation method according to claim 1, wherein step 1 comprises:
after the restrictive hydrolysis treatment is completed, dialyzing a hydrolysate resulting from the restrictive hydrolysis treatment at 0-4° C. for more than 48 h, wherein a cutoff molecular weight of an adopted dialysis bag is above 5000 Daltons, then mixing a dialyzed product with ethanol to obtain an ethanol mixture so that a final concentration of ethanol in the ethanol mixture is 10-25%,
centrifuging the ethanol mixture to remove a precipitate, and
subjecting a supernate to freeze drying and then oven-drying at 75-90° C. for 5-20 min to obtain the polypeptide.

4. The preparation method according to claim 1, wherein the proteases comprise at least one selected from the group consisting of trypsin, alkaline protease, and neutral protease.

5. The preparation method according to claim 1, wherein in step 1, after the restrictive hydrolysis treatment, a hydrolysis degree of the polypeptide obtained is 6.7%-10%.

6. The preparation method according to claim 1, wherein in step 1, a molecular weight of the polypeptide is 5-20 kDa.

7. The preparation method according to claim 1, wherein step 2 comprises:
dispersing the polypeptide and the quercetin into water to form the first mixed system, wherein a concentration of the polypeptide is 10-50 mg/mL and a mass ratio of the quercetin to the polypeptide is 1:100-1:10,
adding NaCl to adjust an ionic strength of the first mixed system to 80-120 mmol/L, then adjusting a pH of the first mixed system to 10-12, and stirring the first mixed system for 30-60 min, so that the polypeptide and the quercetin are subjected to the self-assembling to form the micelle nanoparticle.

8. The preparation method according to claim 1, wherein step 3 comprises:
mixing a solution of the micelle nanoparticle with a solution of the anthocyanin to form the second mixed system,
adjusting a pH of the second mixed system to 9.0-9.5, and continuously stirring the second mixed system at a speed of 300-600 rpm to undergo the covalent grafting reaction for 20-30 h to form the graft.

9. The preparation method according to claim 8, wherein in step 3, a mass ratio of the quercetin to the anthocyanin is 1:2-2:1.

10. The preparation method according to claim 1, wherein step 3 comprises:
after the covalent grafting reaction is completed, adjusting a pH of a reaction mixture to be neutral, and then dialyzing the reaction mixture at 0-4° C. for 20-24 h to obtain the graft, wherein a cutoff molecular weight of an adopted dialysis bag is 3500-4000 Daltons.

11. The preparation method according to claim 1, wherein step 4 comprises: stirring and mixing a solution of the graft with a solution of the carboxymethyl dextrin to obtain a third mixed system, and meanwhile adding an acidic solution to adjust a pH of the third mixed system to obtain the starch-based double-loaded functional nanoparticle.

12. The preparation method according to claim 1, wherein a mass ratio of the polypeptide to the carboxymethyl dextrin is 4:1-1:4.

13. The preparation method according to claim 1, wherein a method for preparing the carboxymethyl dextrin comprises:
alkalizing dextrin with a homogeneous polymerization degree at 35-40° C. for 3-5 h to obtain alkalized dextrin; and
etherifying a mixture containing the alkalized dextrin and monochloroacetic acid in a mass ratio of 1:0.3-1 at 40-45° C. at a pH of 6.5-7.5 for 4-6 h to obtain homogeneous carboxymethyl dextrin with a substitution degree of 0.3-0.7.

14. The preparation method according to claim 13, wherein a method for preparing the dextrin with the homogeneous polymerization degree Comprises:
a) dispersing rice starch into a phosphate buffer solution with a pH of 5-6 to obtain a rice starch dispersion,
b) heating the rice starch dispersion to obtain a gelatinized rice starch and cooling the gelatinized rice starch to 50-55° C. to obtain a cooled gelatinized rice starch,
c) adding pullulanase to the cooled gelatinized rice starch to perform a debranching treatment for 20-24 h, wherein an addition amount of the pullulanase is 50-100 U/g rice starch,
d) subjecting a product obtained in step c to a water bath treatment, then grading the product obtained after the water bath treatment using an ethanol stepwise precipitation method to obtain the dextrin with the homogeneous polymerization degree of 60-80.

15. A starch-based double-loaded functional nanoparticle, wherein the starch-based double-loaded functional nanoparticle is prepared by the preparation method according to claim 1.

16. The starch-based double-loaded functional nanoparticle according to claim 15, wherein the starch-based double-loaded functional nanoparticle is spherical, with a core-shell structure, and possesses a particle size of 189-259 nm and an absolute ζ potential value of 26.1-35.2 mV.

* * * * *